United States Patent
Koltermann

(10) Patent No.: US 10,202,421 B2
(45) Date of Patent: Feb. 12, 2019

(54) TUMOR-TARGETING COMPOUNDS

(71) Applicant: SKU Asset Management GmbH, Baierbrunn (DE)

(72) Inventor: Andre Koltermann, Icking (DE)

( * ) Notice: Subject to any disclaimer, the term of this patent is extended or adjusted under 35 U.S.C. 154(b) by 0 days.

(21) Appl. No.: 15/255,847

(22) Filed: Sep. 2, 2016

(65) Prior Publication Data

US 2017/0096452 A1 Apr. 6, 2017

Related U.S. Application Data

(63) Continuation of application No. 13/144,416, filed as application No. PCT/EP2010/000162 on Jan. 14, 2010.

(30) Foreign Application Priority Data

Jan. 14, 2009 (EP) ..................................... 09000406

(51) Int. Cl.
| | | |
|---|---|---|
| *C07K 7/08* | (2006.01) | |
| *C07K 7/06* | (2006.01) | |
| *A61K 47/64* | (2017.01) | |
| *A61K 38/00* | (2006.01) | |

(52) U.S. Cl.
CPC ............... *C07K 7/08* (2013.01); *A61K 47/64* (2017.08); *A61K 47/646* (2017.08); *C07K 7/06* (2013.01); *A61K 38/00* (2013.01)

(58) Field of Classification Search
CPC ................ C07K 2317/76; C07K 16/18; C07K 2317/31; C07K 2317/73; C07K 2319/70; C07K 14/705; C07K 16/2863; A61K 2039/572
See application file for complete search history.

(56) References Cited

U.S. PATENT DOCUMENTS 8,470,963 B2 * 6/2013 Koltermann ............. C07K 7/06
530/300

FOREIGN PATENT DOCUMENTS

| EP | 2387421 A1 | 11/2011 |
|---|---|---|
| JP | 2012515144 A | 7/2012 |
| WO | WO-2007/001457 A2 | 1/2007 |
| WO | WO-2007/069068 A2 | 6/2007 |
| WO | WO-2007/098466 A2 | 8/2007 |
| WO | WO-2008/000517 A2 | 1/2008 |
| WO | WO-2010/089019 A1 | 8/2010 |

OTHER PUBLICATIONS

Kumar et al. 111In-labeled galectin-3-targeting peptide as a SPECT agent for imaging breast tumors. J Nucl Med. May 2008;49(5):796-803. doi: 10.2967/jnumed.107.048751. Epub Apr. 15, 2008. (Year: 2008).*

(Continued)

*Primary Examiner* — Marcela M Cordero Garcia
*Assistant Examiner* — Jia-Hai Lee
(74) *Attorney, Agent, or Firm* — Ballard Spahr LLP

(57) ABSTRACT

The invention relates to a novel compounds targeting human cancer cells, a method for synthesis of such compounds, and use of such compounds in treating cancer.

16 Claims, 8 Drawing Sheets

Specification includes a Sequence Listing.

(56) References Cited

OTHER PUBLICATIONS

International Search Report dated May 27, 2010 by the International Searching Authority for Application No. PCT/EP2010/000162, which was filed on Jan. 14, 2010 and published as WO/2010/089019 on Aug. 12, 2010 (Applicant—SKU Asset Management GMBH et al; Inventor—Andre Koltermann) (11 Pages).
Written Opinion dated May 27, 2010 by the International Searching Authority for Application No. PCT/EP2010/000162, which was filed on Jan. 14, 2010 and published as WO/2010/089019 on Aug. 12, 2010 (Applicant—SKU Asset Management GMBH et al; Inventor—Andre Koltermann) (11 Pages).
International Preliminary Report on Patentability dated Jul. 19, 2011 by the International Searching Authority for Application No. PCT/EP2010/000162, which was filed on Jan. 14, 2010 and published as WO/2010/089019 on Aug. 12, 2010 (Applicant—SKU Asset Management GMBH et al; Inventor—Andre Koltermann) (8 Pages).
Preliminary Amendment dated Jul. 13, 2011 to the U.S. Patent and Trademark Office for U.S. Appl. No. 13/144,416, filed Jul. 13, 2011 and published as US 2012-0010153 A1 on Jan. 12, 2012 (Inventor—Andre Koltermann) (7 Pages).
Preliminary Amendment dated Sep. 21, 2011 to the U.S. Patent and Trademark Office for U.S. Appl. No. 13/144,416, filed Jul. 13, 2011 and published as US 2012-0010153 A1 on Jan. 12, 2012 (Inventor—Andre Koltermann) (23 Pages).
Requirement for Restriction/Election dated Dec. 27, 2013 by the U.S. Patent and Trademark Office for U.S. Appl. No. 13/144,416, filed Jul. 13, 2011 and published as US 2012-0010153 A1 on Jan. 12, 2012 (Inventor—Andre Koltermann) (9 Pages).
Response to Requirement for Restriction/Election dated Sep. 5, 2014 to the U.S. Patent and Trademark Office for U.S. Appl. No. 13/144,416, filed Jul. 13, 2011 and published as US 2012-0010153 A1 on Jan. 12, 2012 (Inventor—Andre Koltermann) (10 Pages).
Requirement for Restriction/Election dated Jun. 10, 2015 by the U.S. Patent and Trademark Office for U.S. Appl. No. 13/144,416, which was filed on Jul. 13, 2011 and published as US 2012-0010153 A1 on Jan. 12, 2012 (Inventor—Andre Koltermann) (6 Pages).
Response to Requirement for Restriction/Election dated Oct. 13, 2015 to the U.S. Patent and Trademark Office for U.S. Appl. No. 13/144,416, filed Jul. 13, 2011 and published as US 2012-0010153 A1 on Jan. 12, 2012 (Inventor—Andre Koltermann) (3 Pages).
Non Final Rejection dated Mar. 4, 2016 by the U.S. Patent and Trademark Office for U.S. Appl. No. 13/144,416, filed Jul. 13, 2011 and published as US 2012-0010153 A1 on Jan. 12, 2012 (Inventor—Andre Koltermann) (5 Pages).
Abandonment dated Sep. 22, 2016 by the U.S. Patent and Trademark Office for U.S. Appl. No. 13/144,416, filed Jul. 13, 2011 and published as US 2012-0010153 A1 on Jan. 12, 2012 (Inventor—Andre Koltermann) (2 Pages).
Notification of Reasons for Refusal dated Feb. 21, 2014 by the Japan Patent Office for JP Application No. 2011-544849, which was filed on Jan. 14, 2010 and published as JP2012515144A on Jul. 5, 2012 (Original—4 Pages // Translated—3 Pages).
Decision of Refusal dated Jul. 24, 2014 by the Japan Patent Office for JP Application No. 2011-544849, which was filed on Jan. 14, 2010 and published as JP2012515144A on Jul. 5, 2012 (Original—1 Page // Translated—1 Page).

\* cited by examiner

```
                              SEQUENCE LISTING

<160> NUMBER OF SEQ ID NOS: 41

<210> SEQ ID NO 1
<211> LENGTH: 12
<212> TYPE: PRT
<213> ORGANISM: artificial sequence
<220> FEATURE:
<223> OTHER INFORMATION: synthetic construct

<400> SEQUENCE: 1

Tyr His Trp Tyr Gly Tyr Thr Pro Gln Asn Val Ile
1               5                   10

<210> SEQ ID NO 2
<211> LENGTH: 9
<212> TYPE: PRT
<213> ORGANISM: artificial sequence
<220> FEATURE:
<223> OTHER INFORMATION: synthetic construct

<400> SEQUENCE: 2

Cys Ser Asp Ser Trp His Tyr Trp Cys
1               5

<210> SEQ ID NO 3
<211> LENGTH: 9
<212> TYPE: PRT
<213> ORGANISM: artificial sequence
<220> FEATURE:
<223> OTHER INFORMATION: synthetic construct

<400> SEQUENCE: 3

Cys Ser Asp His Trp His Tyr Trp Cys
1               5

<210> SEQ ID NO 4
<211> LENGTH: 9
<212> TYPE: PRT
<213> ORGANISM: artificial sequence
<220> FEATURE:
<223> OTHER INFORMATION: synthetic construct

<400> SEQUENCE: 4

Cys Ser Asp Tyr Asn His His Trp Cys
1               5

<210> SEQ ID NO 5
<211> LENGTH: 9
<212> TYPE: PRT
<213> ORGANISM: artificial sequence
<220> FEATURE:
<223> OTHER INFORMATION: synthetic construct

<400> SEQUENCE: 5

Cys Ser Asp Trp Gln His Pro Trp Cys
1               5
```

```
<210> SEQ ID NO 6
<211> LENGTH: 6
<212> TYPE: PRT
<213> ORGANISM: artificial sequence
<220> FEATURE:
<223> OTHER INFORMATION: synthetic construct

<400> SEQUENCE: 6

Lys Cys Cys Tyr Ser Leu
1               5

<210> SEQ ID NO 7
<211> LENGTH: 7
<212> TYPE: PRT
<213> ORGANISM: artificial sequence
<220> FEATURE:
<223> OTHER INFORMATION: synthetic construct

<400> SEQUENCE: 7

Met Gln Leu Pro Leu Ala Thr
1               5

<210> SEQ ID NO 8
<211> LENGTH: 8
<212> TYPE: PRT
<213> ORGANISM: artificial sequence
<220> FEATURE:
<223> OTHER INFORMATION: synthetic construct

<400> SEQUENCE: 8

Cys Asp Gly Leu Gly Asp Asp Cys
1               5

<210> SEQ ID NO 9
<211> LENGTH: 8
<212> TYPE: PRT
<213> ORGANISM: artificial sequence
<220> FEATURE:
<223> OTHER INFORMATION: synthetic construct

<400> SEQUENCE: 9

Cys Asp Gly Trp Gly Pro Asn Cys
1               5

<210> SEQ ID NO 10
<211> LENGTH: 8
<212> TYPE: PRT
<213> ORGANISM: artificial sequence
<220> FEATURE:
<223> OTHER INFORMATION: synthetic construct

<400> SEQUENCE: 10

Cys Leu Asp Trp Asp Leu Ile Cys
1               5

<210> SEQ ID NO 11
<211> LENGTH: 7
<212> TYPE: PRT
<213> ORGANISM: artificial sequence
<220> FEATURE:
<223> OTHER INFORMATION: synthetic construct

<400> SEQUENCE: 11

Ser Trp Lys Leu Pro Pro Ser
1               5
```

```
<210> SEQ ID NO 12
<211> LENGTH: 9
<212> TYPE: PRT
<213> ORGANISM: artificial sequence
<220> FEATURE:
<223> OTHER INFORMATION: synthetic construct

<400> SEQUENCE: 12

Cys Pro Leu Asp Ile Asp Phe Tyr Cys
1               5

<210> SEQ ID NO 13
<211> LENGTH: 16
<212> TYPE: PRT
<213> ORGANISM: artificial sequence
<220> FEATURE:
<223> OTHER INFORMATION: synthetic construct

<400> SEQUENCE: 13

Ala Asn Thr Pro Cys Gly Pro Tyr Thr His Asp Cys Pro Val Lys Arg
1               5                   10                  15

<210> SEQ ID NO 14
<211> LENGTH: 12
<212> TYPE: PRT
<213> ORGANISM: artificial sequence
<220> FEATURE:
<223> OTHER INFORMATION: synthetic construct

<400> SEQUENCE: 14

Tyr Leu Phe Ser Val His Trp Pro Pro Leu Lys Ala
1               5                   10

<210> SEQ ID NO 15
<211> LENGTH: 7
<212> TYPE: PRT
<213> ORGANISM: artificial sequence
<220> FEATURE:
<223> OTHER INFORMATION: synthetic construct

<400> SEQUENCE: 15

Ser Asp Ser Trp His Tyr Trp
1               5

<210> SEQ ID NO 16
<211> LENGTH: 7
<212> TYPE: PRT
<213> ORGANISM: artificial sequence
<220> FEATURE:
<223> OTHER INFORMATION: synthetic construct

<400> SEQUENCE: 16

Ser Asp His Trp His Tyr Trp
1               5

<210> SEQ ID NO 17
<211> LENGTH: 7
<212> TYPE: PRT
<213> ORGANISM: artificial sequence
<220> FEATURE:
<223> OTHER INFORMATION: synthetic construct

<400> SEQUENCE: 17

Ser Asp Tyr Asn His His Trp
1               5
```

```
<210> SEQ ID NO 18
<211> LENGTH: 7
<212> TYPE: PRT
<213> ORGANISM: artificial sequence
<220> FEATURE:
<223> OTHER INFORMATION: synthetic construct

<400> SEQUENCE: 18

Ser Asp Trp Gln His Pro Trp
1               5

<210> SEQ ID NO 19
<211> LENGTH: 6
<212> TYPE: PRT
<213> ORGANISM: artificial sequence
<220> FEATURE:
<223> OTHER INFORMATION: synthetic construct

<400> SEQUENCE: 19

Asp Gly Leu Gly Asp Asp
1               5

<210> SEQ ID NO 20
<211> LENGTH: 6
<212> TYPE: PRT
<213> ORGANISM: artificial sequence
<220> FEATURE:
<223> OTHER INFORMATION: synthetic construct

<400> SEQUENCE: 20

Asp Gly Trp Gly Pro Asn
1               5

<210> SEQ ID NO 21
<211> LENGTH: 6
<212> TYPE: PRT
<213> ORGANISM: artificial sequence
<220> FEATURE:
<223> OTHER INFORMATION: synthetic construct

<400> SEQUENCE: 21

Leu Asp Trp Asp Leu Ile
1               5

<210> SEQ ID NO 22
<211> LENGTH: 7
<212> TYPE: PRT
<213> ORGANISM: artificial sequence
<220> FEATURE:
<223> OTHER INFORMATION: synthetic construct

<400> SEQUENCE: 22

Pro Leu Asp Ile Asp Phe Tyr
1               5

<210> SEQ ID NO 23
<211> LENGTH: 6
<212> TYPE: PRT
<213> ORGANISM: artificial sequence
<220> FEATURE:
<223> OTHER INFORMATION: synthetic construct

<400> SEQUENCE: 23

Gly Pro Tyr Thr His Asp
1               5

<210> SEQ ID NO 24
```

```
<211> LENGTH: 2
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 24

Met Leu
1

<210> SEQ ID NO 25
<211> LENGTH: 3
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 25

Met Leu Pro
1

<210> SEQ ID NO 26
<211> LENGTH: 3
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 26

Met Leu Phe
1

<210> SEQ ID NO 27
<211> LENGTH: 4
<212> TYPE: PRT
<213> ORGANISM: artificial sequence
<220> FEATURE:
<223> OTHER INFORMATION: synthetic construct

<400> SEQUENCE: 27

Tyr His Trp Tyr
1

<210> SEQ ID NO 28
<211> LENGTH: 4
<212> TYPE: PRT
<213> ORGANISM: artificial sequence
<220> FEATURE:
<223> OTHER INFORMATION: synthetic construct

<400> SEQUENCE: 28

His Trp Tyr Gly
1

<210> SEQ ID NO 29
<211> LENGTH: 4
<212> TYPE: PRT
<213> ORGANISM: artificial sequence
<220> FEATURE:
<223> OTHER INFORMATION: synthetic construct
```

```
<400> SEQUENCE: 29

Trp Tyr Gly Tyr
1

<210> SEQ ID NO 30
<211> LENGTH: 4
<212> TYPE: PRT
<213> ORGANISM: artificial sequence
<220> FEATURE:
<223> OTHER INFORMATION: synthetic construct

<400> SEQUENCE: 30

Tyr Gly Tyr Thr
1

<210> SEQ ID NO 31
<211> LENGTH: 4
<212> TYPE: PRT
<213> ORGANISM: artificial sequence
<220> FEATURE:
<223> OTHER INFORMATION: synthetic construct

<400> SEQUENCE: 31

Gly Tyr Thr Pro
1

<210> SEQ ID NO 32
<211> LENGTH: 4
<212> TYPE: PRT
<213> ORGANISM: artificial sequence
<220> FEATURE:
<223> OTHER INFORMATION: synthetic construct

<400> SEQUENCE: 32

Tyr Thr Pro Gln
1

<210> SEQ ID NO 33
<211> LENGTH: 4
<212> TYPE: PRT
<213> ORGANISM: artificial sequence
<220> FEATURE:
<223> OTHER INFORMATION: synthetic construct

<400> SEQUENCE: 33

Thr Pro Gln Asn
1

<210> SEQ ID NO 34
<211> LENGTH: 4
<212> TYPE: PRT
<213> ORGANISM: artificial sequence
<220> FEATURE:
<223> OTHER INFORMATION: synthetic construct

<400> SEQUENCE: 34

Pro Gln Asn Val
1

<210> SEQ ID NO 35
<211> LENGTH: 4
<212> TYPE: PRT
<213> ORGANISM: artificial sequence
<220> FEATURE:
<223> OTHER INFORMATION: synthetic construct
```

```
<400> SEQUENCE: 35

Gln Asn Val Ile
1

<210> SEQ ID NO 36
<211> LENGTH: 6
<212> TYPE: PRT
<213> ORGANISM: artificial sequence
<220> FEATURE:
<223> OTHER INFORMATION: synthetic construct

<400> SEQUENCE: 36

Tyr Gly Tyr Thr Pro Gln
1               5

<210> SEQ ID NO 37
<211> LENGTH: 8
<212> TYPE: PRT
<213> ORGANISM: artificial sequence
<220> FEATURE:
<223> OTHER INFORMATION: synthetic construct

<400> SEQUENCE: 37

Trp Tyr Gly Tyr Thr Pro Gln Asn
1               5

<210> SEQ ID NO 38
<211> LENGTH: 10
<212> TYPE: PRT
<213> ORGANISM: artificial sequence
<220> FEATURE:
<223> OTHER INFORMATION: synthetic construct

<400> SEQUENCE: 38

His Trp Tyr Gly Tyr Thr Pro Gln Asn Val
1               5                   10

<210> SEQ ID NO 39
<211> LENGTH: 5
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 39

Met Leu Pro Lys Lys
1               5

<210> SEQ ID NO 40
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 40

Met Leu Lys Lys
1

<210> SEQ ID NO 41
<211> LENGTH: 5
```

```
<212> TYPE: PRT
<213> ORGANISM: artificial sequence
<220> FEATURE:
<223> OTHER INFORMATION: synthetic construct
<220> FEATURE:
<221> NAME/KEY: Formylation
<222> LOCATION: (1)..(1)

<400> SEQUENCE: 41

Met Leu Phe Lys Lys
1               5
```

TUMOR-TARGETING COMPOUNDS

CROSS-REFERENCES TO RELATED APPLICATIONS

This application is a Continuation of U.S. application Ser. No. 13/144,416, filed Jul. 13, 2011, which is a U.S. National Stage of International Application No. PCT/EP2010/000162, filed Jan. 14, 2010, which designated the United States and has been published as International Publication No. WO 2010/089019 and which claims the priority of European Patent Application, Serial No. 09000406.0, filed Jan. 14, 2009, pursuant to 35 U.S.C. 119(a)-(d).

BACKGROUND OF THE INVENTION

The invention relates to novel compounds targeting tumor markers; a method for synthesis of such compound; and use of such compound in treating cancer.

There is a strong need for the development of new anti-cancer therapies, in particular for chemotherapeutic agents that target specifically cancer cells.

Several such therapies rely on immunotoxins, i.e. compounds that are conjugates of toxic drugs to antibody molecules or protein ligands to receptors on human cancer cells. For example, antibodies that attach to cancer cells are used as conjugates with toxins in an attempt to minimize any delivery of the toxin to non-pathogenic cells. Immunotoxins have been developed e.g. by linking tumor-specific antibodies to Ricin, *Pseudomonas* exotoxin, Diptheria toxin, and Tumor necrosis factor alpha (TNF-a).

The described approaches have significant disadvantages, e.g. in terms of unspecific toxicity, low efficacy, and high cost of manufacturing. Consequently, there is a need to provide anti-tumor compounds that are specific for tumor cells and that can be manufactured at lower costs. In particular, there is a need to provide compounds with anti-tumor efficacy and specificity that can be manufactured entirely by chemical synthesis from standard chemical building blocks.

Such synthetic compounds with anti-tumor efficacy and specificity have been described in a general form in WO2008/000517 which is included here as reference. There is a need to further improve such compounds.

SUMMARY OF THE INVENTION

It is the objective of the present invention to provide novel synthetic compounds which enable an effective treatment of tumor cells. This objective is accomplished by the idea of providing simple chemically synthesized compounds, the structure and function of which is based on the structure and function of immunoglobulins. The invention specially provides compounds and methods as specified in the claims below.

Specifically, the invention provides compounds with anti-tumor efficacy that are conjugates comprised of a backbone structure and one or more synthetic binders, whereby the backbone structure is a synthetic chemical structure that comprises one or more effector functions, flexible linker structures, as well as one or more coupling sites for the binders. Preferably, the effector functions within the backbone structure act as ligands to pathogen pattern recognition receptors (PRRs), in particular comprising pathogen-associated molecular patterns (PAMPS), and/or activates PRRs.

In a preferred embodiment of the invention, the backbone structure resembles the Y structure of immunoglobulins with the effector function at the base of the compound and two flexible arms where the binders are located (see FIG. 1). Therefore, the compound comprises one branching point between flexible linker structures (the arms) as in immunoglobulins or in further embodiments additional branching points. The coupling sites for the binders are located at the end of such flexible linker structures.

In a further embodiment, the invention provides compounds that specifically target tumor cell markers. Preferably, such tumor cell markers include human Epidermal Growth Factor Receptor (EGFR); human Vascular Endothelia Growth Factor Receptor (VEGFR); ErbB-2 receptor (Her-2); Fibroblast Growth Factor Receptor (FGFR); integrins, including alpha-3-beta-1 integrin and alpha-4-beta-1 integrin; lectins, including human beta-galactoside-binding lectin 3 (Galectin-3, or Gal-3); c-Met (hepatocyte growth factor receptor, HGFR or scatter factor, SF).

In particular the invention provides a compound that comprises, two or more binders (resembling the head portion of the immunoglobulin structure); a backbone structure comprising at least one coupling site for the binder, at least one linker structure, and at least one effector (to resemble the base of the immunoglobulin structure), whereby the effector comprises one of the following sequences: SEQ ID NO 24; fML (N-formyl-Met-Leu); SEQ ID NO 25 fMLP (N-formyl-Met-Leu-Pro); SEQ ID NO 26 fMLF (N-formyl-Met-Leu-Phe), and whereby the linker structure is composed of a polypeptide, of polyethylene glycol, or a combination thereof.

Definitions

The term "binder" as used in the present invention preferably refers to any molecular structure, which interacts/binds with a second molecular structure, in particular with a tumor marker on a target tumor cell. The binder of the invention can be of natural or synthetic origin and be modified or unmodified. Binders of the present invention include small molecules, peptides, peptide mimetics, modified or unmodified amino acids, oligonucleotides, as well as fragments, derivatives, analogs, chimerics or polymers of the aforementioned. Other examples of binders include synthetically produced small molecules. The term small molecule preferably refers to a bioactive molecule with preferably a molecular weight of below 500 Da. Small molecules are molecules other than peptides, proteins, DNA or RNA.

The term "tumor marker" as used in the present invention refers to any structure which is sufficiently specific for cancer cells, therewith enabling their discrimination from other host structures. Any structure which is capable of distinguishing host structures from cancer cells either quantatively or qualitatively can serve as a tumor marker, as e.g. in the case of overexpressed cell surface proteins that are also present on other host cells, but in lower quantity. The interactions between binders and tumor markers can comprise any kind of chemical or physical interaction, e.g. hydrogen bonds, van-der-Waals forces or hydrophobic interactions. The specificity of the marker can be due either to its selective expression or its enhanced expression in or on or at the proximity of cancer cells. Examples for tumor markers include receptors, ion channels and other cell-surface proteins.

The term "effector" preferably refers to any molecular structure which modulates signal transduction via a PRR. The effectors of the present invention include small molecules, saccharides, peptides, peptide mimetics, natural or other amino acids, oligonucleotides as well as fragments, derivatives, analogs, chimerics or polymers thereof. Effectors include lipopolysaccharides, teichoic acids, nucleotides with unmethylated CpG motifs, double-stranded RNA, mannans, and formyl peptides. One important function of the effectors can be the immune cell activation. Effectors are preferably angonist of PRR, i.e. they induce or otherwise enhance the signal transduction activity of the receptor. Effectors especially include molecular structures that have direct or indirect stimulatory, modifying or activating effects on the innate immune system. Cells of the innate immune system are effective in destroying and removing pathogens as well as diseased tissues or cells. Cells of the innate immune system that are activated by effectors include macrophages, neutrophils including polymorphonuclear neutrophils, lymphocytes and NK cells.

The term "linker structure" preferably refers to any structure which is able to physically link two molecular entities whereby these entities can exhibit their intended function. Linkers can be composed of a variety of chemical structures, for example, polyethylene glycols, peptides, ethers, esters.

The term "activation" when used in combination with cells or receptors (and quantitative measurement or qualitative assessment thereof) preferably refers to any direct or indirect immune response, including, for example, infiltration, degranulation, rolling, chemotaxis, phagocytosis, endocytosis, increased expression or activity of various catabolic or degradative enzymes (e.g., elastases), oxidative burst, production or release of hydrogen peroxide and other highly reactive oxygen species, intracellular calcium flux, cell polarization, and changes in inositol metabolism and signaling. Other determinants of activation include increased expression and production of leukotrienes, complement, chemokines, cytokines, chemoattractant factors, interleukins, or interferons. Methods for measuring these activities are well known to those skilled in the art. (See e.g., William E. Paul, Fundamental Immunology, Lippincott Williams and Wilking Publishers. 1999; John E. Coligen et al., Current Protocols in Immunology, John Wiley & Sons, New York, N.Y., 1999.)

The term "substantially homologous", when used in connection with amino acid sequences, preferably refers to sequences which are substantially identical to or similar in sequence, giving rise to a homology in conformation and thus to similar biological activity. The term is not intended to imply a common evolution of the sequences. Typically "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications". Generally, to determine the percent homology of two sequences, the sequences are aligned for optimal comparison purposes (e.g., gaps can be introduced in one or both of a first and a second sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first sequence which has for example 100 residues, at least 30, preferably at least 40, more preferably at least 50, even more preferably at least 60, and even more preferably at least 70, 80 or 90 residues are aligned).

The term "non-immunoglobulin" refers to a synthetic molecule that is not a natural immunoglobulin or a natural immunoglobulin with a synthetic portion. However, according to the invention the molecule more or less resembles the general structure of an immunoglobulin.

The term "preferably" is meant to suggest alternatives to the invention and not to limit or restrict the invention in any way.

Amino acid abbreviations: A: Ala, Alanine; C: Cys, Cysteine; D: Asp, Aspartic acid; E: Glu, Glutamic acid; F: Phe, Phenylalanine; G: Gly, Glycine; H: His, Histidine; I: Ile, Isoleucine; K: Lys, Lysine; L: Leu, Leucine; M: Met, Methionine; N: Asn, Asparagine; P: Pro, Proline; Q: Gln, Glutamine; R: Arg, Arginine; S: Ser, Serine; T: Thr, Threonine; V: Val, Valine; W: Trp, Tryptophan; Y: Tyr, Tyrosine; X: any amino acid.

DETAILED DESCRIPTION OF PREFERRED EMBODIMENTS

As outlined above, the present invention provides novel compounds which enable an effective treatment of tumor cells.

This objective is accomplished by providing anti-tumor compounds that are conjugates comprised of a backbone structure and one or more synthetic binders, whereby the backbone structure is a synthetic chemical structure that comprises one or more effectors, one or more flexible linker structures, as well as one or more coupling sites for the binders.

The backbone structure of the inventive compound provides the basic functions of the compound, i.e. (i) the effector function, (ii) sites to which binders can be coupled, and (iii) a flexible framework to enable interaction of the compound with both, cells of the innate immune system as well as with target cells bearing tumor markers. Besides these functions the backbone structure is preferably selected to have no other side activity.

Figure 1:
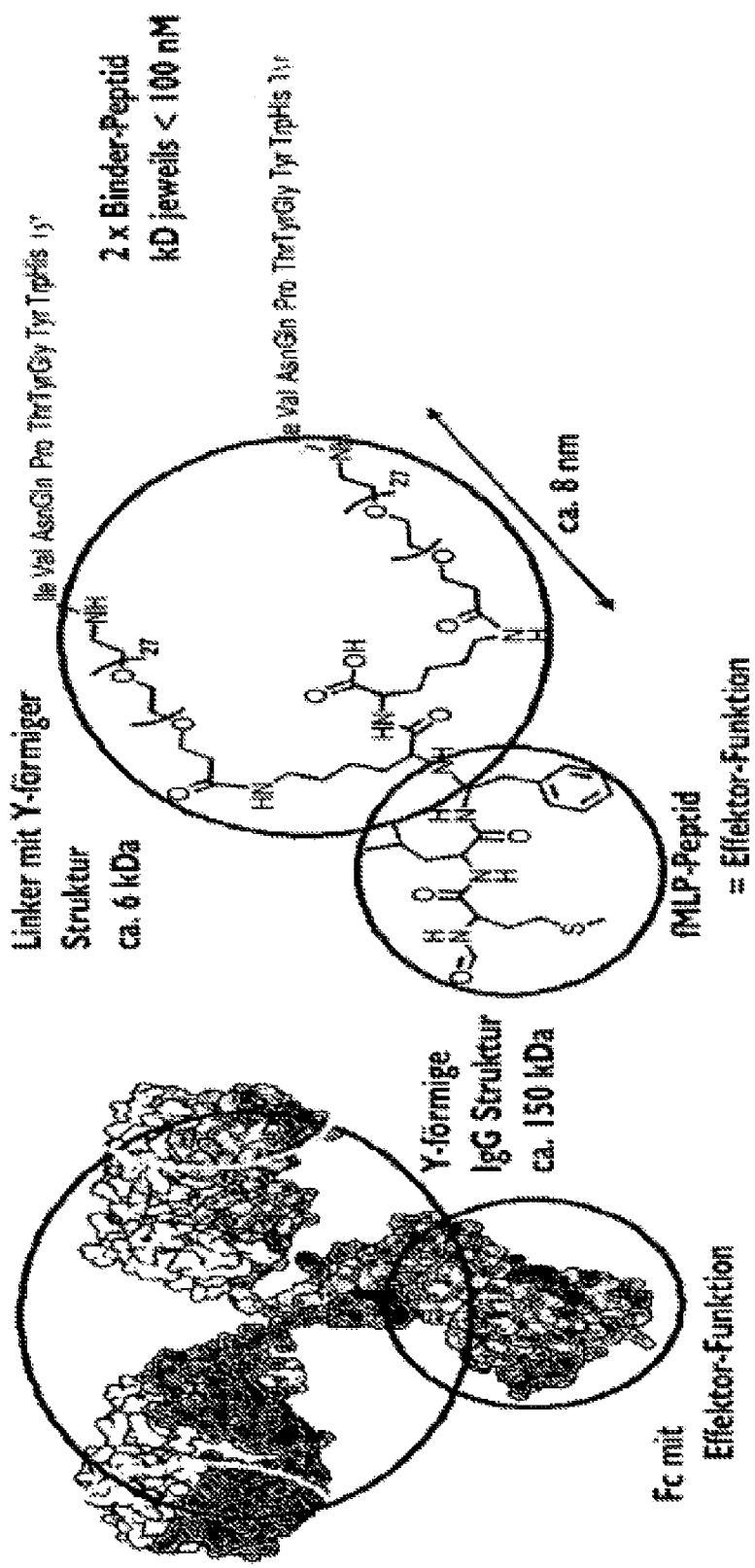
FIG. 1: Comparison of functionalities, size and intramolecular distances of the inventive compound with the structure of an immunoglobulin

The backbone structure preferably resembles in size and function the structure of an immunoglobulin G, i.e. (i) the effector function is located at the base of an Y-shaped structure like the Fc part of an immunoglobulin G; (ii) Two (or more) flexible linker structures are attached to the base via branching points like the Fab fragments in an immunoglobulin G; (iii) The binders are attached to the end of the flexible linker structures like the CDRs which are located at the tips of the Fab fragments in an immunoglobulin G. The length of the flexible linkers when they are completely extended can be approximately 8 nm. This is in the same range as the length of an Fab fragment thereby providing the ability to bind to two binding sites (e.g. receptors on the surface of a cell) located in the same distance as immunoglobulins (see FIG. 1).

The at least one effector within the backbone structure is any substance which can act as a ligand to a pathogen pattern recognition receptor (PRR), in particular substances that comprise pathogen-associated molecular patterns (PAMPS), and/or activate PRRs, to exhibit at least one of their biological functions within the innate immune system. The innate immune system represents a defense mechanism that recognizes a few highly conserved structures present in many different pathogens. Such pathogen-associated molecular patterns include LPS from the gram-negative bacterial cell wall, peptidoglycans, lipotechoic acids from the gram-positive bacterial cell wall, the sugar mannose common in many microbial glycolipids and glycoproteins, fucose, N-acetyl glucosamine, bacterial DNA, N-formylmethionine found in bacterial proteins, double-stranded RNA from viruses, and glucans from fungal cell walls.

The targeted PRRs of the invention include inter glia mannose receptors (MR), formyl peptide receptors (FPRs), toll-like receptors (TLRs), CD14, and nucleotide-binding oligomerization domain proteins (NOD). Binding of ligands to these receptors also promotes the synthesis and secretion of intracellular regulatory molecules (immune modulating signals) such as cytokines that are crucial to initiating innate immunity and adaptive immunity. Examples for effectors of the present invention are peptides, formylated peptides, in particular N-formyl methionine peptides, peptidoglycans, acylated lipopeptides, e.g. diacylated mycoplasmal lipopeptides or triacylated bacterial lipopeptide and tryacyl lipopeptide (Pam3CSSNA), diaminopimelic acid containing desmuramyi peptide (gamma-D-glutamyl-meso-DAP; iE-DAP), and muramyldipeptide (MDP), CpG containing nucleotides, dsRNA, oligo- or polycarbohydrates containing mannose, fucose, lacto-N-fucopentaose III (LNFPIII), imidazoquinolines, phosphocholine.

In one embodiment of the invention the at least one effector activates a formyl peptide receptor (FPR). Activation of FPRs leads to several phases of neutrophil response and activation, including chemoattraction, stimulation of production and release of immunosignaling molecules (e.g., interleukins, cytokines, etc.), as well as degranulation, a cellular process that includes the production and release of both chemical (e.g., hydrogen peroxide and other reactive oxygen radical species) and enzymatic agents (e.g., elastase and other digestive enzymes) capable of mediating destruction of the foreign agent or pathogen. In humans, three related FPR family members have been identified: the eponymous formyl peptide receptor (FPR), as well as two other receptors, FPRL1 and FPRL2. FPRL1 and FPRL2 are related to FPR by sequence homology but appear to be functionally distinct. The cellular response mediated by the formyl peptide receptor (FPR) includes cellular polarization and transmigration, generation of superoxide O2 radicals through respiratory burst oxidase, degranulation and release of a variety of various degradative enzymes, as well as phagocytosis. According to the invention the effector interacts with the FPR and therewith induces at least one of the above mentioned cellular responses.

In a preferred aspect of this embodiment the effector contains N-formyl methionine residues. More preferably, the effector comprises one of the following N-terminal amino acid sequences: N-formyl-methionine-leucine (SEQ ID NO 24, fML); N-formyl-methionine-leucine-phenylalanine (SEQ ID NO 26, fMLF); N-formyl-methionine-leucine-proline (SEQ ID NO 25, fMLP). Particularly preferred effectors are the peptides formyl-methionylleucine (SEQ ID NO 24, N-formyl-Met-Leu; fML), formyl-methionylleucylphenylalanine (SEQ ID NO 26, N-formyl-Met-Leu-Phe; fMLF), and formyl-methionylleucylproline (SEQ ID NO 25, N-formyl-Met-Leu-Pro; fMLP). Formylmethionyl peptides are proinflammatory peptides which are able to stimulate many leukocyte functions. They stimulate neutrophil chemotaxis, lysosomal enzyme release, oxygen-free radical production, Ca++ flux, leukotriene release by neutrophils and smooth muscle contraction. Formylmethionine stimulation of neutrophils induces rapid alterations in their expression of adhesion receptors. In addition, formylmethionyl peptides have been shown to induce superoxide production and an increase in intracellular Ca++ levels. Formylmethionyl peptides have been shown to induce chemotaxis in a number of cells, including pulmonary alveolar macrophages, neutrophils, dendritic cells (DC) and monocytes. In fact, the chemotactic or chemoattractant activity of formylmethionyl peptides is sufficiently well established that fMLF is often used as a positive control in chemotactic assays. The cellular response mediated by binding of formylated peptide antagonists to the formyl peptide receptor (FPR) includes cellular polarization and transmigration, generation of superoxide O2 radicals through respiratory burst oxidase, degranulation and release of a variety of various degradative enzymes, as well as phagocytosis.

The flexible linkers within the backbone structure of the inventive compound are preferably selected to enable the compound to interact with different cell surface proteins. Furthermore, the chemistry of the backbone structure is preferably selected to have no or very low immunogenicity in the human body. Furthermore, the size of the backbone structure is preferably adjusted through the length of the linkers. Preferably the size of the inventive compound is selected in a range to facilitate tissue penetration of the compound and/or to adjust the clearance of the compound from the human body to its therapeutic efficacy.

Examples of such linkers include oligomers and polymers of ethylene glycol (PEG), peptides, dendrimers, e.g. polylysine, oligonucleotides comprised of ribonucleic acid (RNA), desoxynucleic acid (DNA), peptide nucleic acids (PNA), polysaccharides, e.g. hydroyethylcellulose or hydroxyethyl starch, dextrans, aminodextrans, polyethers, polyamides, polyesters, polyurethanes.

In a preferred embodiment of the invention one or more flexible linkers within the backbone structure are composed of oligomers or polymers of ethylene glycol. Polyethylene glycol is known to have no or very low immunogenicity in the human body. The size of the backbone structure is adjusted by selecting the number of ethylene units used to synthesize the polyethylene glycol linkers. Preferably the number of ethylene glycol units within the backbone structure is in the range between 1 and 250, more preferably between 1 and 100. In a particularly preferred aspect of this embodiment the number of ethylene glycol units is in the range between 20 and 80.

In another preferred embodiment of the invention one or more flexible linkers within the backbone structure are composed of peptide sequences, i.e. oligomers of amino acids. Such oligomers can be homooligomers (e.g. polylysine, polyglycine, etc.) or can be composed of different amino acids, including standard as well as non-standard amino acids. Preferably the number of amino acid residues within the backbone structure that form flexible linker units is in the range between 1 and 100, more preferably between 1 and 50. In a particularly preferred embodiment the number of amino acids residues is in the range between 10 and 25. In a further, particularly preferred embodiment the peptide oligomers have the sequence (GGGGS).sub.2-4, i.e. the sequence GGGGS is repeated 2 to 4 times. Such linkers typically form flexible structures in aqueous solution. In a another, particularly preferred embodiment the peptide oligomers have the sequence (EAAAK).sub.2-5, i.e. the sequence EAAAK is repeated 2 to 5 times. Such linker typically form alpha-helical structures in aqueous solution.

Furthermore, the backbone structure of the inventive compound comprises coupling sites that can be used to covalently link binder moieties to the backbone structure. Any chemical residue can be used as coupling site which enables site-specific covalent linking of binder moieties to the backbone structure. Examples of such chemical residues include a carboxylic acid group, an activated carboxyl group (e.g. active ester), an amino group, an aldehyde, an isocyanate, a thiol group, a maleimide, a succinimidyl ester.

In a preferred embodiment of the invention the coupling site is an amino group and the one or more binder moieties are covalently coupled to the backbone structure via an activated carboxyl group. In a particularly preferred embodiment the coupling sites are amino groups and the one or more binder moieties are peptides which are covalently coupled with the C terminal alpha carboxyl group to the amino group at the coupling site, thereby providing a compound comprising one or more peptide binders with free N termini.

The backbone structure preferably further comprises branching points to enable the introduction of either more than one effector, or more than one coupling site, or both. In a preferred embodiment of the invention the backbone structure comprises at least one branching point and at least two coupling sites, and flexible linkers are included between the at least one branching point and the at least two coupling sites.

Examples of branching points include trifunctional monomers such as the amino acids lysine, ornithine and citrulline (one carboxyl group and two amino groups), aspartic acid and glutamic acid (two carboxyl groups and one amino group), cystein (one carboxyl group, one amino group, and one thiol group), or tricarboxylic acids such as citric acid, isocitric acid or aconitic acid (three carboxyl groups), as well as tetrafunctional monomers such as lanthionine (two carboxyl groups and two amino groups).

In a particularly preferred embodiment of the invention the backbone structure comprises two or more amino acids with an additional amino side group (such as lysine, ornithine or citrulline) as branching points whereby these amino acids are linked by peptide bonds to each other and whereby one of the resulting three or more amino groups (one alpha amino group and two or more other amino groups) serves as coupling site for the effector and the remaining two or more amino groups serve as coupling sites for the binders. In a further, particularly preferred aspect of this embodiment the single resulting alpha amino group serves as coupling site for the effector and the two or more other amino groups serve as coupling sites for the binders. Preferably, between one or more of the effectors, branching points and/or binders a flexible linker is synthesized.

Accordingly, in a particularly preferred embodiment of the invention the backbone structure has one of the following compositions:

Variant 1:

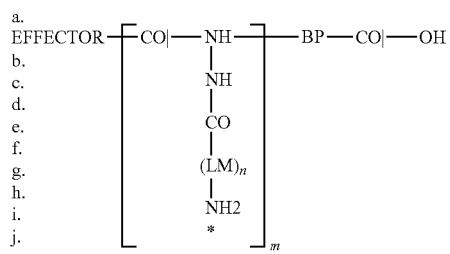

Variant 2:

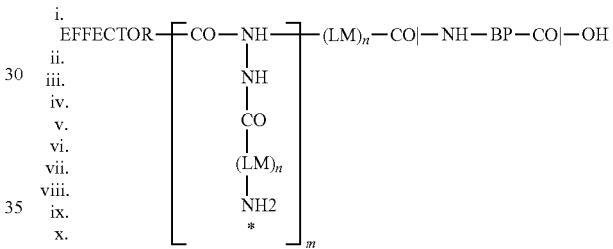

wherein "EFFECTOR" is an effector moiety, "CO—NH" or "NH—CO" symbolizes a peptide bond, "LM" is a linker monomer (e.g. ethylene glycol, or an amino acid), "BP" is a branching point (e.g. a lysine residue), "NH2" is an amino group, "OH" is a hydroxyl group, and "n" and "m" are integers. The asterisk "*" marks the coupling sites at which the binders are covalently coupled to the backbone structure.

In a preferred aspect of this embodiment, n is between 1 and 100, more preferably between 10 and 50, and even more preferably between 15 and 35. In a particularly preferred embodiment n is 27. Preferably m is lower than or equal 10, more preferably lower than or equal 5, and even more preferably m is 2 or 3. In a particularly preferred embodiment m is 2.

The backbone structure can be manufactured completely by chemical synthesis. In one embodiment of the invention, the backbone structure is completely synthesized by solid-phase synthesis. Standard protocols for solid phase synthesis of peptides can be used to synthesize the backbone structure of the inventive compound. In a preferred embodiment of the invention the backbone structure is synthesized starting with an amino acid having two amino acid groups (a branching point, e.g. lysine) which is coupled with the carboxyl group to a solid support (e.g. polystyrene). Thereby, the linker structure as well the effector can be coupled to the molecule via activated carboxyl groups. In a further preferred aspect of this embodiment the one or more effectors and/or the one or more linker structures are peptides and are synthesized by coupling the respective amino acid residues via activated carboxyl esters to the molecule.

The binders are covalently linked to the synthetic backbone structure via the coupling sites. In one embodiment the inventive compound is manufactured by synthesizing the backbone structure via solid phase synthesis followed by coupling of the binder moieties to the backbone structure. In another preferred embodiment of the invention the one or more binders are peptides, and the inventive compound is completely synthesized by solid phase synthesis.

Examples of binders according to the invention are peptides (linear, cyclic, or branched), peptide mimetics, peptide repeats, oligonucleotides (e.g. DNA, RNA), oligonucleotide analogs (e.g. PNA, DNA/RNA chimera, etc.) or small molecules.

In a particular embodiment of the invention the binder is peptide. Preferably the length of the peptide is between 1 and 75 amino acid residues, more preferably between 3 and 25 amino acid residues. In a preferred embodiment of the invention the binders are peptides comprising specific amino acid sequences. Such sequences can contain the 20 standard amino acids, non-standard amino acids, as well as chemically modified amino acids. Examples of non-standard amino adds include carnitine, citrulline, homoarginine, homocitrulline, homocysteine, homophenylalanine, homoproline, hydroxyproline, allo-isoleucine, isoserine, ornithine, phenylglycine, phenylisoserine, allo-threonine, selenocysteine, pyrrolysine, lanthionine, 2-amino isobutyric acid, gamma-amino butyric acid, dehydroalanine (2-amino acrylic acid), beta alanine (3-amino propanoic acid, or a stereo-isomer thereof. The peptide sequences can comprise both, L-amino acids as well as D-amino acids.

In a further preferred embodiment of the invention the one or more binders are cyclic structures. In a particularly preferred embodiment the binders are cyclic peptides. Peptides of 30 or less amino acids are often unstructured in aqueous solutions. These peptides adopt a defined conformation only upon complex formation with partner molecules such as a receptor. Unstructured peptides can be metabolically unstable due to faster clearance from the mammalian body. Stability, bioavailability as well as selectivity for interaction with receptors can be increased by cyclization of such peptides.

In one embodiment cyclic peptides are generated by intramolecular disulfide bridging. It has been shown that peptides with intramolecular disulfide bridges are conformationally stable and thereby can be highly selective binders, e.g. for receptors. Examples of such peptides are defensins (pathogen control in vertebrates and invertebrates).

In another embodiment cyclic peptides are generated by stably linking the N and the C terminus of the peptide (head-to-tail cyclization) by forming an amide bond between the amino- and the carboxy-terminus. This bond formation leads to homodetic, cyclic peptides. The coupling chemistry used therefore is based on activated esters similar to the chemistry applied during solid phase peptide synthesis.

In a further embodiment of the invention, cyclic peptides are generated by side chain-to-side chain cyclization. This leads to macrocyclic structures with thioether, lactam, lactone or carbon-carbon linkages upon reaction between appropriate functional groups. In a particularly preferred aspect of this embodiment a thiol side chain (e.g. of a cystein residue) reacts with the C—C double bond (e.g. of a 2-amino acrylic acid residue) to form a thioether bond. In another particularly preferred aspect of this embodiment two C—C double bonds (e.g. of 2-amino acrylic acid residues) react to form a carbon-carbon double bond linkage between the two amino acid residues. Such homo- and heterodetic peptide macrocycles can be equipped with additional functional groups such as aldehydes, ketones and aminooxy groups as handles for covalent attachment to the coupling site in the backbone structure.

In a another preferred embodiment the stabilities of binder and/or effector peptides are increased and/or the peptides are protected from proteolytic degradation by blocking the amino and/or carboxy termini. The term blocking refers to the introduction of a blocking group to the terminus of the peptide via a covalent modification. Suitable blocking groups do not interfere with the biological activity of the peptides. Acetylation of the amino termini of the peptides is a preferred method of protecting the peptides from proteolytic degradation. Preferred blocking moieties comprise the following acyl moieties (in the order of increasing hydrophobicity): formyl, acetyl, propanoyl, hexanoyl. Amidation of the carboxy termini of the peptides is a further preferred method of protecting the peptides from proteolytic degradation.

In a preferred embodiment of the invention, compounds are provided that comprise one or more binders, whereby the binders bind to one of the following tumor markers: human Epidermal Growth Factor Receptor (EGFR); human Vascular Endothelia Growth Factor Receptor (VEGFR); ErbB-2 receptor (Her-2); Fibroblast Growth Factor Receptor (FGF receptor); Integrins including Alpha-3-beta-1 Integrin and Alpha-4-beta-1 Integrin; human beta-galactoside-binding lectin Galectin-3 (Gal-3); c-Met (Receptor for human Hepatocyte Growth Factor, HGF, or Scatter Factor, SF).

Such binders preferably comprise one of the following sequences SEQ ID NO 1, YHWYGYTPQNVI; SEQ ID NO 2, CSDSWHYWC; SEQ ID NO 3, CSDHWHYWC; SEQ ID NO 4, CSDYNHHWC; SEQ ID NO 5, CSDWQHPWC; SEQ ID NO 6, KCCYSL; SEQ ID NO 7, MQLPLAT; SEQ ID NO 8, CDGLGDDC; SEQ ID NO 9, CDGWGPNC; SEQ ID NO 10, CLDWDLIC; SEQ ID NO 11, SWKLPPS; SEQ ID NO 12, CPLDIDFYC; SEQ ID NO 13, ANTPCGPYTHDCPVKR; SEQ ID NO 14, YLFSVHWPPLKA; or a fragment thereof with a length of at least four amino acid residues. Preferably, the peptide binders are covalently linked to the backbone structure via the C terminus in order to provide compounds with binders that have free N termini.

In another preferred aspect of this embodiment the invention the binders comprise one of the following sequences: SEQ ID NO 15, SDSWHYW; SEQ ID NO 16, SDHWHYW; SEQ ID NO 17, SDYNHHW; SEQ ID NO 18, SDWQHPW; SEQ ID NO 19, DGLGDD; SEQ ID NO 20, DGWGPN; SEQ ID NO 21, LDWDLI; SEQ ID NO 22, PLDIDFY; SEQ ID NO 23, GPYTHD in a homo- or heterodetic peptide macrocycle which is formed through a thioether or a C—C double bond.

In a particular aspect of this embodiment the invention provides compounds of the structure type: (Binder-Linker1) n-Linker2-Effector, wherein the Binder is a peptide and comprises one of the following sequences SEQ ID NO 1, YHWYGYTPQNVI; SEQ ID NO 2, CSDSWHYWC; SEQ ID NO 3, CSDHWHYWC; SEQ ID NO 4, CSDYNHHWC; SEQ ID NO 5, CSDWQHPWC; SEQ ID NO 6, KCCYSL; SEQ ID NO 7, MQLPLAT; SEQ ID NO 8, CDGLGDDC; SEQ ID NO 9, CDGWGPNC; SEQ ID NO 10, CLDWDLIC; SEQ ID NO 11, SWKLPPS; SEQ ID NO 12, CPLDIDFYC; SEQ ID NO 13, ANTPCGPYTHDCPVKR; SEQ ID NO 14, YLFSVHWPPLKA; or a fragment thereof with a length of at least four amino acid residues; the Effector is a peptide and comprises one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe);
Linker1 and Linker2 are a polypeptide, a polyethylene glycol structure, or combination thereof, or a single covalent bond; n is at least 2.

In a further preferred embodiment of the invention, compounds are provided that comprise one or more binders which are operably linked to at least one effector, whereby the binders bind to human Epidermal Growth Factor Receptor (EGFR) and/or related markers on tumor cells, and whereby the at least one effector is any substance which can act as a ligand to a pathogen pattern recognition receptor (PRR), in particular substances that comprise pathogen-associated molecular patterns (PAMPS), and/or activate PRRs. Such compounds can preferably be used in the treatment of solid tumors, in particular for the treatment of colon, breast, prostate, head & neck, NSCLC, ovarian, bladder, and/or esophageal cancer.

In particular the invention provides a compound that comprises two or more peptides as binders, each comprising one of the following sequences: SEQ ID NO 27, YHWY; SEQ ID NO 28, HWYG; SEQ ID NO 29, WYGY; SEQ ID NO 30, YGYT; SEQ ID NO 31, GYTP; SEQ ID NO 32, YTPQ; SEQ ID NO 33, TPQN; SEQ ID NO 34, PQNV; SEQ ID NO 35, QNVI; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); and
linker molecules composed of a polypeptide, of polyethylene glycol, or of a combination thereof, or of a single covalent bond, whereby the linker molecules covalently link the two or more binders to the at least one effector.

In a preferred embodiment the invention provides a compound that comprises two or more peptides as binders comprising the sequence SEQ ID NO 1, YHWYGYTPQNVI (Tyr-His-Trp-Tyr-Gly-Tyr-Thr-Pro-Gln-Asn-Val-Ile) or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

Alternatively, the binder peptide sequence, SEQ ID NO 1, YHWYGYTPQNVI could be replaced by a variation thereof (truncated or single amino acid residues replaced) as well as by other peptide sequences providing binding capability to EGFR.

The binder peptide sequence can be attached alternatively via its N terminus or its C terminus.

Furthermore the invention provides compounds of the structure type: (Binder-Linker1)n-Linker2-Effector, wherein the Binder is a peptide and comprises the sequence, SEQ ID NO 1, YHWYGYTPQNVI (Tyr-His-Trp-Tyr-Gly-Tyr-Thr-Pro-Gln-Asn-Val-lie) or a fragment thereof with a length of at least four amino acid residues; the Effector is a peptide and comprises one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); Linker1 and Linker2 are a polypeptide, a polyethylene glycol structure, or combination thereof, or a single covalent bond; n is at least 2 and signifies the number of binder molecules bound to the effector.

Preferably, such compounds comprise binders that are peptides with a length between 3 and 75 amino acid residues, more preferably between 4 and 25 amino acid residues, and comprise the sequence, SEQ ID NO 1, YHWYGYTPQNVI (Tyr-His-Trp-Tyr-Gly-Tyr-Thr-Pro-Gln-Asn-Val-Ile), or a fragment thereof with a length of at least four amino acid residues, preferably SEQ ID NO 36, YGYTPQ; SEQ ID NO 37, WYGYTPQN; or SEQ ID NO 38, HWYGYTPQNV, or a peptide that is substantially homologous to the sequence SEQ ID NO 1, YHWYGYTPQNVI or a fragment thereof. Therefore, the binder in such compounds is a peptide that comprises at least one of the following sequences: SEQ ID NO 27, YHWY; SEQ ID NO 28, HWYG; SEQ ID NO 29, WYGY; SEQ ID NO 30, YGYT; SEQ ID NO 31, GYTP; SEQ ID NO 32, YTPQ; SEQ ID NO 33, TPQN; SEQ ID NO 34, PQNV; SEQ ID NO 35, QNVI, or a sequence that is substantially homologous to one of these sequences.

In a particular aspect of this embodiment, the peptide has binding affinity to human EGFR (Epidermal Growth Factor Receptor) and/or variants, derivatives or homologues thereof. For example, the oligopeptide has binding affinity to the full-length EGFR or to the truncated receptor EGFRvIII (Epidermal Growth Factor Receptor variant III) or to both. EGFR is overexpressed in a number of pathogenic cell populations such as in colon cancer, head and neck cancer, ovarial cancer, pancreatic cancer, non-small cell lung cancer, breast cancer and glioblastoma.

In a preferred embodiment of the invention, a compound is provided having the formula: (Binder-Linker)n-Effector, wherein the Binder is a peptide comprising the sequence, SEQ ID NO 1, YHWYGYTPQNVI (Tyr-His-Trp-Tyr-Gly-Tyr-Thr-Pro-Gln-Asn-Val-Ile) or a fragment thereof with a length of at least four amino acid residues;
the Effector is a peptide comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe) at the N terminus as well as n lysine residues; the n Linker molecules are polyethylene glycol oligomers; the Effector is covalently attached via the epsilon amino groups of the n lysine residues through an amide bond to terminal carboxy groups of the n Linker molecules; the Binder molecules are covalently attached via the carboxy terminus through an amide bond to a terminal carboxy group of the polyethylene glycol Linker; n is an integer between 2 and 10.

In another preferred embodiment of the invention, a compound is provided having the formula: (Binder-Linker)2-Effector, wherein;
the Binder is a peptide with the sequence, SEQ ID NO 1, YHWYGYTPQNVI (Tyr-His-Trp-Tyr-Gly-Tyr-Thr-Pro-Gln-Asn-Val-Ile); the Effector is a peptide comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe) at the N terminus as well as two lysine residues; the two Linker molecules are polyethylene glycol oligomers; the Effector is covalently attached via the epsilon amino groups of the two lysine residues through an amide bond to terminal carboxy groups of the two Linker molecules; the Binder molecules are covalently attached via the carboxy terminus through an amide bond to a terminal carboxy group of the polyethylene glycol Linker molecules.

In another preferred embodiment of the invention, a compound is provided having the formula: (Binder-Linker)2-Effector, wherein the Binder is a peptide with the sequence, SEQ ID NO 1, YHWYGYTPQNVI (Tyr-His-Trp- Tyr-Gly-Tyr-Thr-Pro-Gln-Asn-Val-Ile); the Effector is a peptide comprising the sequence SEQ ID NO 39, fMLPKK (N-formyl-Met-Leu-Pro-Lys-Lys); the two Linker molecules are polyethylene glycol oligomers with a length between 2 and 100 ethylene glycol units; the Effector is covalently attached via the epsilon amino groups of the two lysine residues through an amide bond to terminal carboxy groups of the two Linker molecules; the Binder molecules are covalently attached via the carboxy terminus through an amide bond to a terminal carboxy group of the polyethylene glycol Linker molecules.

Figure 2:
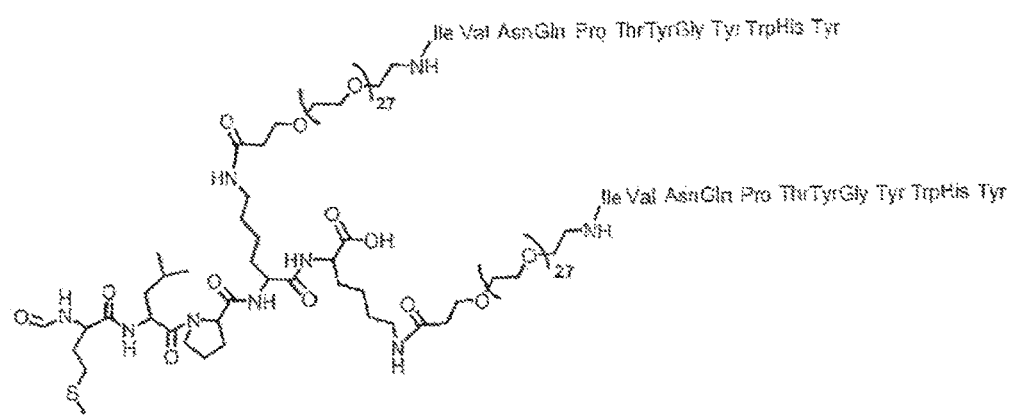
FIG. 2: Structure 1 according to a preferred embodiment of the invention, with two binder peptides comprising the peptide sequence, SEQ ID NO 1 YHWYGYTPQNVI, one effector comprising the peptide sequence, SEQ ID NO 25 fMLP, and PEG as linker.

In another embodiment of the invention, a compound is provided having the structure 1 as shown in FIG. 2 (FIG. 2: Structure 1 according to a preferred embodiment of the invention).

Figure 3:
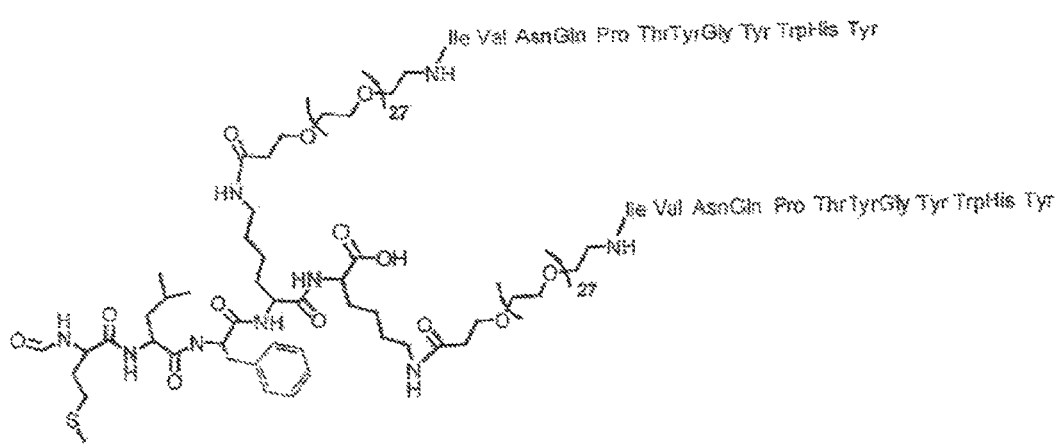
FIG. 3: Structure 2 according to a preferred embodiment of the invention, with two binder peptides comprising the peptide sequence, SEQ ID NO 1 YHWYGYTPQNVI, one effector comprising the peptide sequence, SEQ ID NO 26 fMLF, and PEG as linker.

In another embodiment of the invention, a compound is provided having the structure 2 as shown in FIG. 3 (FIG. 3: Structure 2 according to a preferred embodiment of the invention).

Figures 4A, 4B:
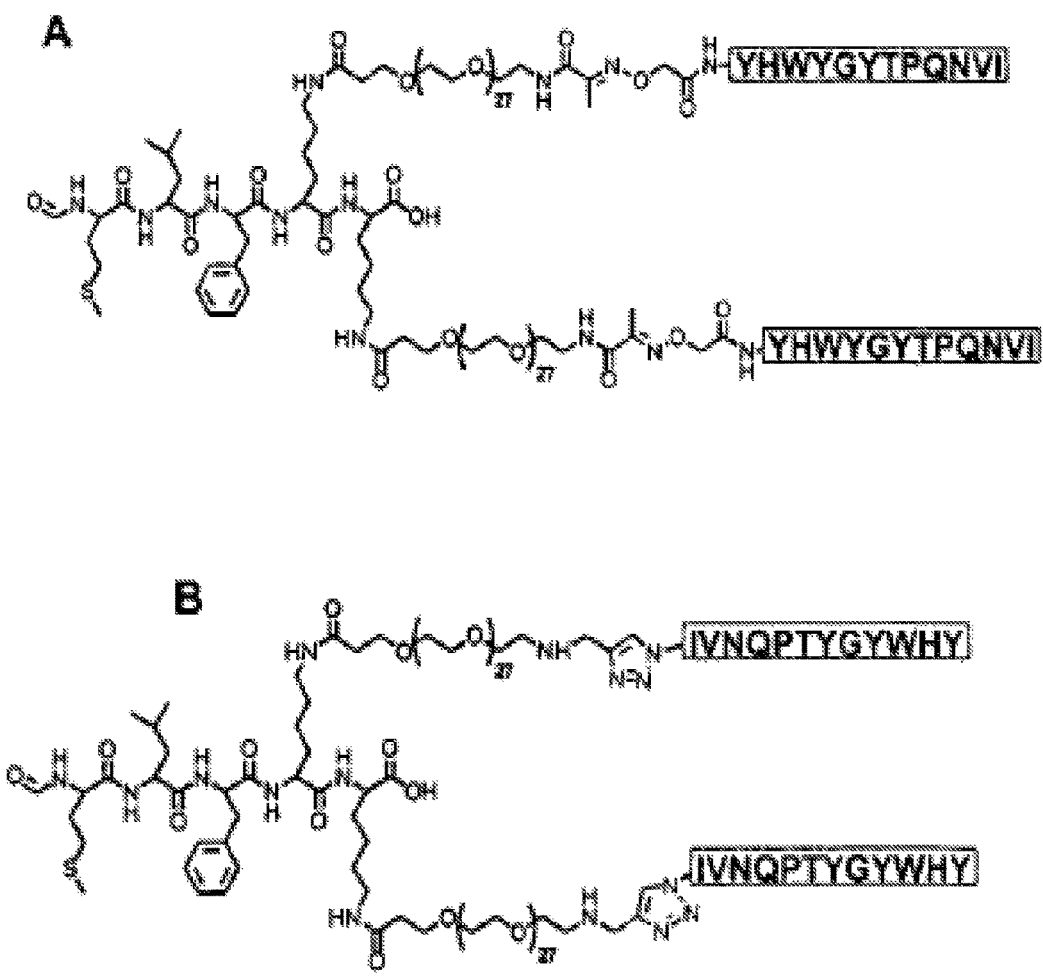
FIG. 4A, FIG. 4B, FIG. 4C FIG. 4D and FIG. 4E: Variations of structure 2 with different chemical structures for coupling the binders to the flexible linker structures. The binder peptide sequence, SEQ ID NO 1 YHWYGYTPQNVI could be replaced by a variation thereof (truncated or single amino acid residues replaced) as well as by other peptide sequences providing binding capability to tumor markers. The binder can be attached via its C terminus (as in structures B and E) or via its N terminus (as in structures A, C and D).
Figures 4C, 4D, 4E:
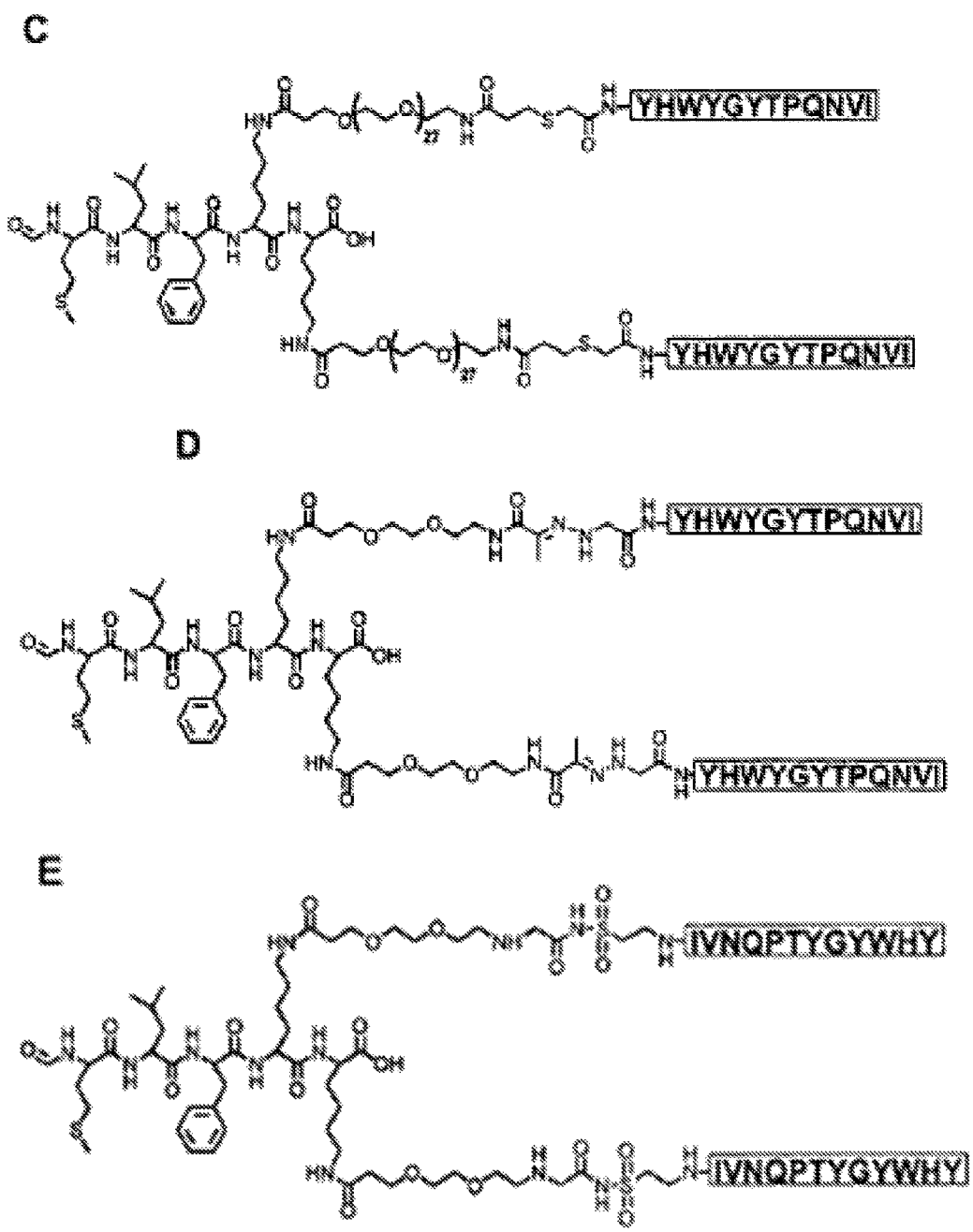

In another embodiment of the invention a compound is provided having one of the structures shown in FIG. 4 (FIG. 4 A-E).

In a further preferred embodiment of the invention, compounds are provided that comprise binders to human Vascular Endothelia Growth Factor Receptor (VEGFR) and/or related markers on tumor cells. Such compounds can be used in the treatment of a variety of human cancers that have a VEGFR or related marker.

In a further preferred embodiment of the invention, the binders bind to human Vascular Endothelia Growth Factor Receptor (VEGFR) and/or related markers on tumor cells, and comprise one of the following sequences: SEQ ID NO 2, CSDHWHYWC; SEQ ID NO 3, CSDHWHYWC; SEQ ID NO 4, CSDYNHHWC; SEQ ID NO 5, CSDWQHPWC; or a fragment thereof with a length of at least four amino acid residues.

In a preferred embodiment the invention provides a compound that comprises two or more peptides as binders comprising the sequence, SEQ ID NO 2, CSDHWHYWC; SEQ ID NO 3, CSDHWHYWC; SEQ ID NO 4, CSDYNHHWC; SEQ ID NO 5, CSDWQHPWC; or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

In a further preferred embodiment the binder comprises the sequence SEQ ID NO 15, SDSWHYW; SEQ ID NO 16, SDHWHYW; SEQ ID NO 17, SDYNHHW; or SEQ ID NO 18, SDWQHPW; and side chain-to-side chain cyclization is carried out via a thioether, lactam, lactone or carbon-carbon linkage upon reaction between appropriate functional groups. Particularly preferred linkages comprise formation of a thioether bond and formation of a carbon-carbon double bond. Such peptide macrocycles can be equipped with additional functional groups such as aldehydes, ketones and aminooxy groups as handles for covalent attachment to the linker molecule.

In a further preferred embodiment of the invention, compounds are provided that comprise binders to human ErbB-2 receptor (Her-2) and/or related markers on tumor cells. Such compounds can preferably be used in the treatment of breast cancer, pancreatic cancer, ovarian cancer, NSCLC and/or lymphoma.

In a further preferred embodiment of the invention, the binders bind to human ErbB-2 receptor (Her-2) and/or related markers on tumor cells, and comprise one of the following sequences: SEQ ID NO 6, KCCYSL, or a fragment thereof with a length of at least four amino acid residues.

In a preferred embodiment the invention provides a compound that comprises two or more peptides as binders comprising the sequence, SEQ ID NO 6, KCCYSL or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

In a further preferred embodiment of the invention, compounds are provided that comprise binders to human Fibroblast Growth Factor Receptor (FGF receptor) and/or related markers on tumor cells. Such compounds can preferably be used in the treatment of Ovarian cancer.

In a further preferred embodiment of the invention, the binders bind to human Fibroblast Growth Factor Receptor (FGF receptor) and/or related markers on tumor cells, and comprise one of the following sequences: SEQ ID NO 7, MQLPLAT; or a fragment thereof with a length of at least four amino acid residues.

In a preferred embodiment the invention provides a compound that comprises two or more peptides as binders comprising the sequence, SEQ ID NO 7, MQLPLAT or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

In a further preferred embodiment of the invention, compounds are provided that comprise binders to human Integrins including Alpha-3-beta-1 Integrin and Alpha-4-beta-1 Integrin and/or related markers on tumor cells. Such compounds can preferably be used in the treatment of multiple peritoneal tumors of gastric cancer.

In a further preferred embodiment of the invention, the binders bind to human Integrins including Alpha-3-beta-1 Integrin and Alpha-4-beta-1 Integrin and/or related markers on tumor cells, and comprise one of the following sequences: SEQ ID NO 8, CDGLGDDC; SEQ ID NO 9, CDGWGPNC; SEQ ID NO 10, CLDWDLIC; SEQ ID NO 11, SWKLPPS; SEQ ID NO 12, CPLDIDFYC; or a fragment thereof with a length of at least four amino acid residues.

In a preferred embodiment the invention provides a compound that comprises two or more peptides as binders comprising the sequence, SEQ ID NO 8, CDGLGDDC; SEQ ID NO 9, CDGWGPNC; SEQ ID NO 10, CLDWDLIC; SEQ ID NO 11, SWKLPPS; SEQ ID NO 12, CPLDIDFYC; or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

In a further preferred embodiment the binder comprises the sequence SEQ ID NO 19, DGLGDD, SEQ ID NO 20, DGWGPN; SEQ ID NO 21, LDWDLI; SEQ ID NO 11, SWKLPPS; or SEQ ID NO 22, PLDIDFY, and side chain-to-side chain cyclization is carried out via a thioether, lactam, lactone or carbon-carbon linkage upon reaction between appropriate functional groups. Particularly preferred linkages comprise formation of a thioether bond and formation of a carbon-carbon double bond. Such peptide macrocycles can be equipped with additional functional groups such as aldehydes, ketones and aminooxy groups as handles for covalent attachment to the linker molecule.

In a further preferred embodiment of the invention, compounds are provided that comprise binders to human beta-galactoside-binding lectin Galectin-3 (Gal-3) and/or related markers on tumor cells. Such compounds can preferably be used in the treatment of breast cancer.

In a further preferred embodiment of the invention, the binders bind to human Integrins including Alpha-3-beta-1 Integrin and Alpha-4-beta-1 Integrin and/or related markers on tumor cells, and comprise one of the following sequences: SEQ ID NO 13, ANTPCGPYTHDCPVKR or a fragment thereof with a length of at least four amino acid residues.

In a preferred embodiment the invention provides a compound that comprises two or more peptides as binders comprising the sequence SEQ ID NO 13, ANTPCGPYTH-DCPVKR; or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

In a further preferred embodiment the binder comprises the sequence SEQ ID NO 23, GPYTHD and side chain-to-side chain cyclization is carried out via a thioether, lactam, lactone or carbon-carbon linkage upon reaction between appropriate functional groups. Particularly preferred linkages comprise formation of a thioether bond and formation of a carbon-carbon double bond. Such peptide macrocycles can be equipped with additional functional groups such as aldehydes, ketones and aminooxy groups as handles for covalent attachment to the linker molecule.

In a further preferred embodiment of the invention, compounds are provided that comprise binders to c-Met (Receptor for human Hepatocyte Growth Factor, HGF, or Scatter Factor, SF) and/or related markers on tumor cells. Such compounds can preferably be used in the treatment of a variety of human tumors.

In a further preferred embodiment of the invention, the binders bind to c-Met (Receptor for human Hepatocyte Growth Factor, HGF, or Scatter Factor, SF) and/or related markers on tumor cells, and comprise one of the following sequences: SEQ ID NO 14, YLFSVHWPPLKA or a fragment thereof with a length of at least four amino acid residues.

In a preferred embodiment the invention provides a compound that comprises two or more peptides as binders comprising the sequence, SEQ ID NO 14, YLFSVHWP-PLKA; or a fragment thereof with a length of at least four amino acid residues; at least one peptide as effector comprising one of the following sequences: SEQ ID NO 24, fML (N-formyl-Met-Leu); SEQ ID NO 25, fMLP (N-formyl-Met-Leu-Pro); SEQ ID NO 26, fMLF (N-formyl-Met-Leu-Phe); an oligomeric linker composed of a polypeptide, of polyethylene glycol, or of a combination thereof, or of a single covalent bond.

EXAMPLES

Example 1 Binding Tests of Structure 1 to EGFR and EGFR-Expressing Cells

The peptide SEQ ID NO 1, YHWYGYTPQNVI showing specific binding activity to the tumor marker Erb-B1/EGFR was chosen as binder and the macrophage-activating peptide formyl-MLP as effector to synthesize structure 1. The structure was synthesized chemically by standard methods known in the art and purified by ion exchange chromatography. Chemical identity was verified by mass spectrometry. Unlike immunoglobulins and other known antitumor compounds, structure 1 demonstrated high solubility at pH 7 (up to 10 mg/ml). Size exclusion chromatography as well as dynamic light scattering analysis showed no oligomers or large aggregates and indicated a hydrodynamic radius slightly larger than expected for a molecule of approximately 6 kDa.

Figures 5A, 5B:
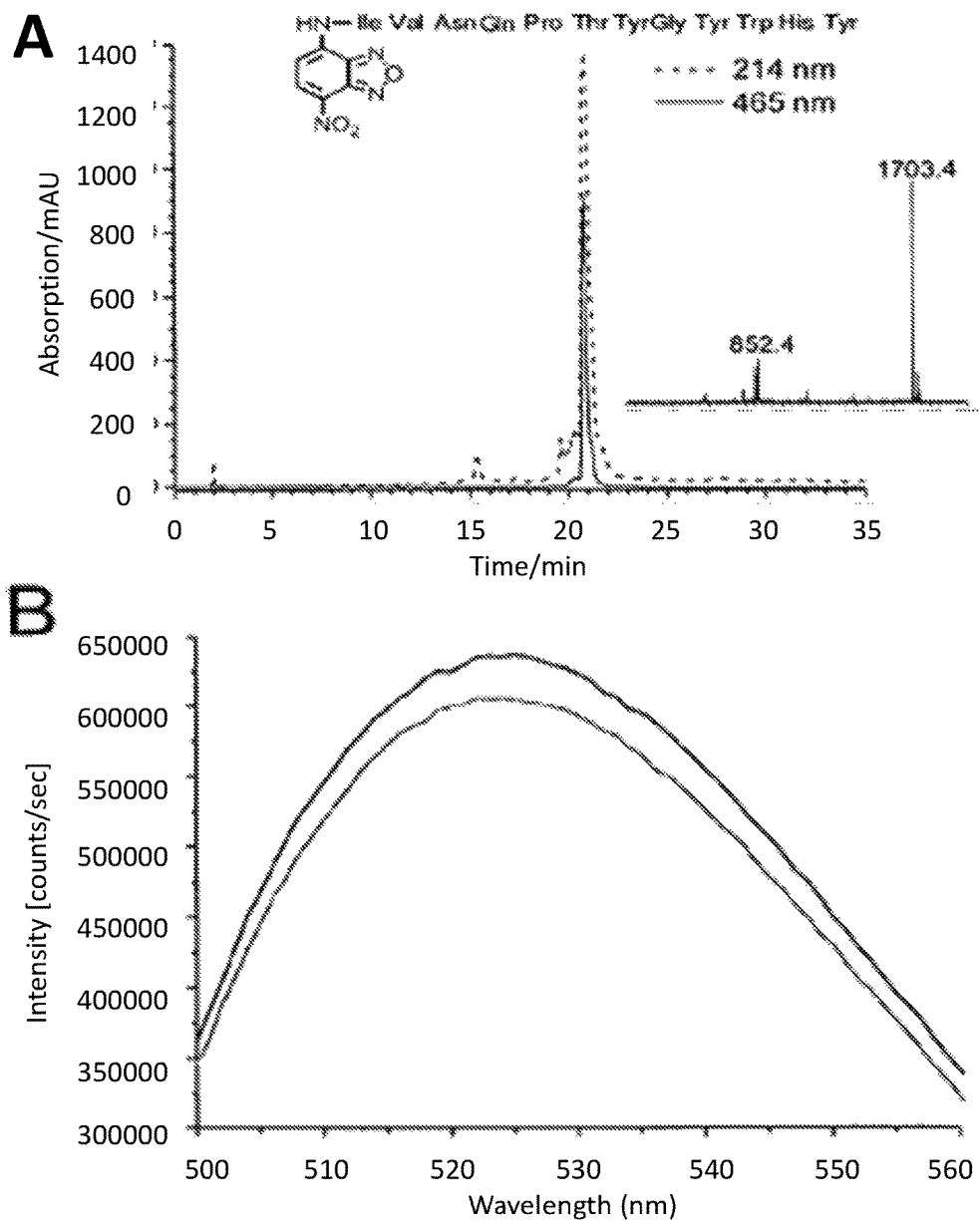
FIG. 5A, FIG. 5B, FIG. 5C, and FIG. 5D: Binding studies with EGFR and the compound according to structure 1.

Binding affinity of structure 1 to human EGFR/Erb-B1 was tested using a fluorescently labelled variant and commercially available EGFR preparations using fluorescence spectroscopy. In these experiments a fluorescently labelled SEQ ID NO 1, YHWYGYTPQNVI 12mer (FIG. 5a) was incubated with EGFR in order to form a complex. Upon addition of structure 1 to the preformed complex a decrease in fluorescence intensity was observed due to displacement of the fluorescent peptide from the complex with EGFR (FIG. 5b). A KD value in the low nM range for the interaction of structure 1 with EGFR was estimated. This finding confirms the notion that multivalency will increase affinity of a binder to the respective receptor. This effect is expected to be relevant when targeting receptors on cell surfaces.

Figure 5C:
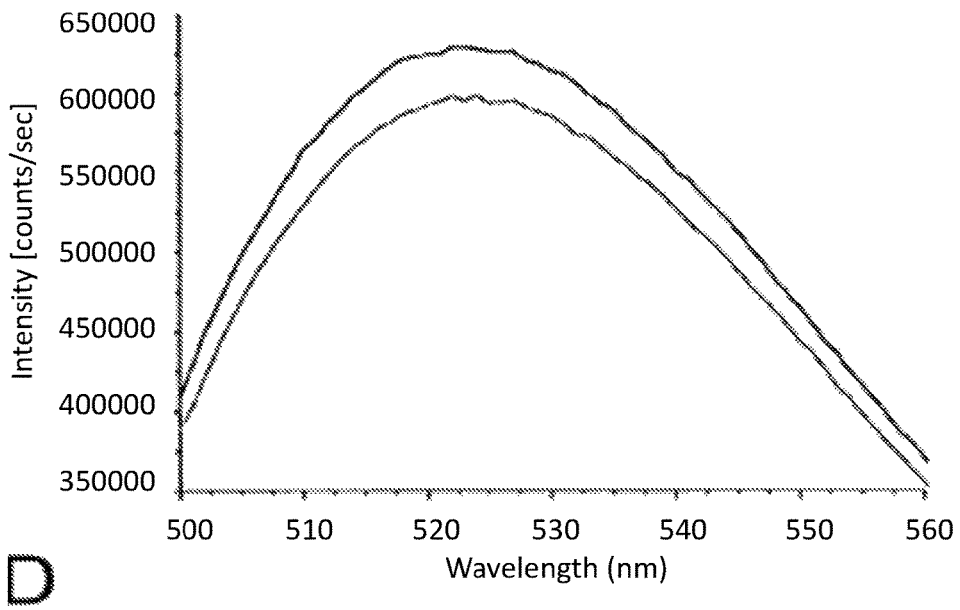
Figure 5D:
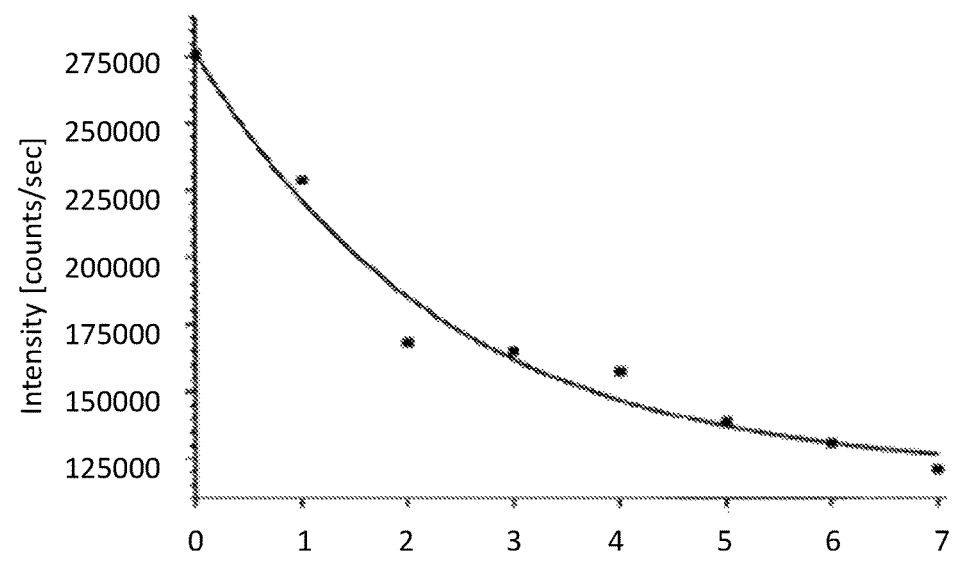

The results are shown in FIG. 5. FIG. 5a shows HPLC and MS data of an NBD-labelled variant of the 12mer EGFR-binding peptide used in displacement experiments as fluorescent tracer. The observed molar mass of 1703.4 Da is in good agreement with the calculated mass. FIG. 5b shows binding of the NBD-labeled tracer peptide to EGFR. 50 nM tracer (grey line) were mixed with 50 nM EGFR. Mixing results in an increase of fluorescence intensity (black line). FIG. 5c shows displacement of the fluorescent tracer peptide from the EGFR complex after adding non-labelled peptide. The EGFR-tracer complex is preformed at 50 nM in PBS buffer at pH 7.5 (black line, excitation at 460 nm). A 10 fold excess of unlabelled peptide is added and the observed decrease in fluorescence intensity (grey line) reflects release of the tracer molecule. FIG. 5d shows displacement with increasing concentrations of structure 1. A 1 .mu.M solution of EGFR and NBD-12mer peptide complex is titrated with increasing concentrations of structure 1 leading to displacement of the fluorescent tracer.

Example 2 Macrophage Activation in a Chemotaxis Assay

In a chemotaxis assay (trans-well assay for macrophage mobilization) the macrophage activation profile of structure 1 and structure 2 and their precursors containing the N-formyl peptide sequence was demonstrated.

Figure 6:
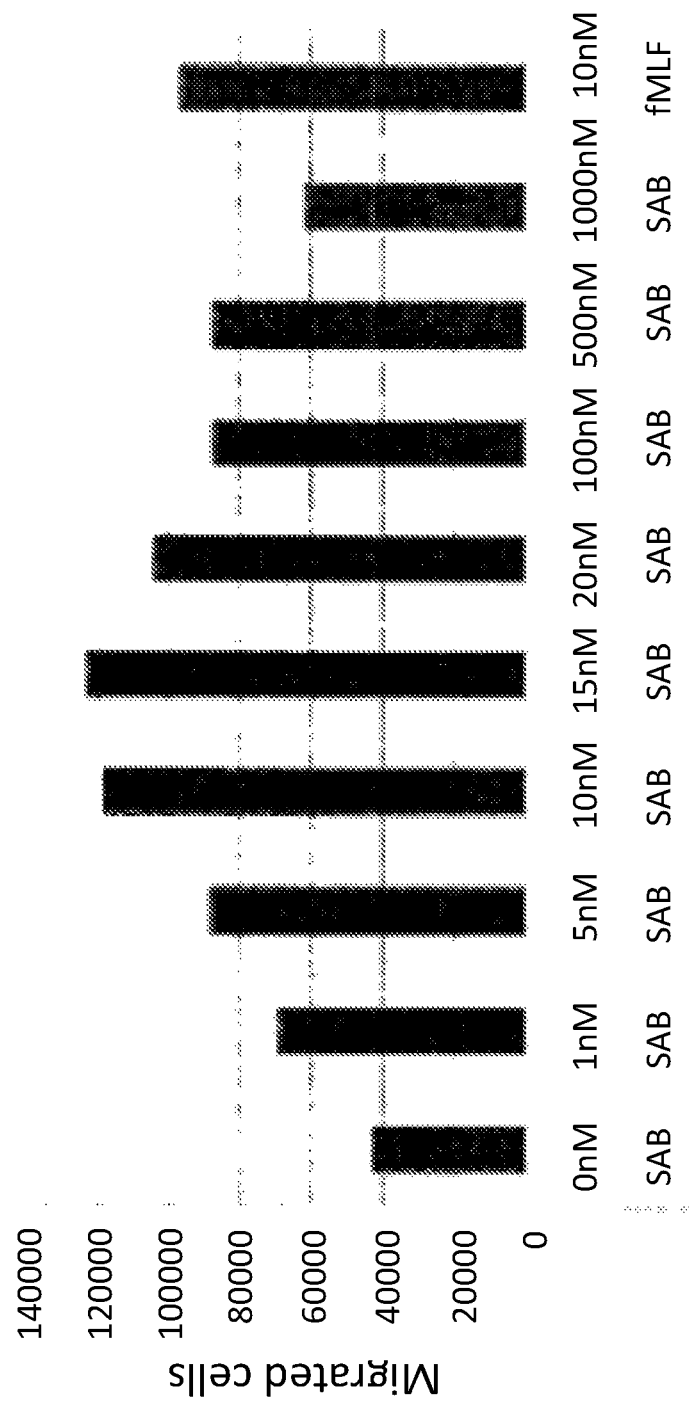
FIG. 6: Chemotaxis assays with the compound according to structure 2. "SAB" refers to the structure 2, "fMLF" refers to a fMLF peptide only used as control.

The results of the chemotaxis assay with structure 2 are shown in FIG. 6. Concentration-dependent granulocyte activation of N-formyl peptide conjugates has been compared with activation of the peptide only. Each series of experiments has been repeated 3 times with 200,000 granulocytes each. The structure 2 compound induces a similar (slightly higher) chemotactic behavior (measured by counting migrated cells in response to stimulus) as the reference N-formyl peptide at the same concentration.

In a separate experiment it has also been demonstrated that granulocyte chemotaxis can be stimulated with both alternatives, the chemotactic response of SEQ ID NO 26 fMLF being slightly higher compared to SEQ ID NO 25 fMLP. Therefore, variations in the formyl peptide amino acid composition, e.g. different amino acid residues at position 3 (phenylalanine, proline) as in structure 1 and structure 2, provide a further means to tune the immune response.

The invention claimed is:

1. A synthetic non-immunoglobulin antitumor compound relating to the structure of an immunoglobulin, the compound comprising, (a) two or more peptides as binders, each consisting of amino acids 5-16 of SEQ ID NO:13; (b) at least one peptide as effector comprising one of the following sequences SEQ ID NO 24; SEQ ID NO 25; SEQ ID NO 26; and (c) at least one linker molecules composed of a polypeptide, of polyethylene glycol, or of a combination thereof, whereby the linker molecules covalently link the two or more binders to the at least one effector to relate to the structure of an immunoglobulin molecule.

2. The antitumor compound according to claim 1 having the formula: (Binder-Linker)2-Effector, wherein (a) the binder peptides consist of amino acids 5-16 of SEQ ID NO:13; (b) the effector peptide comprises one of the following sequences: SEQ ID NO 24; SEQ ID NO 25; SEQ ID NO 26 at the N terminus as well as two lysine residues; (c) the linker molecules are polyethylene glycol oligomers; (d) the effector is covalently attached via the epsilon amino groups of the two lysine residues through an amide bond to terminal carboxy groups of the two linker molecules; (e) the binder molecules are covalently attached via the carboxy terminus through an amide bond to a terminal carboxy group of the polyethylene glycol linker molecules.

3. The antitumor compound according to claim 1 wherein the amino terminal ends of the peptide sequences of the binders are acetylated to increase stability.

4. A pharmaceutical composition comprising a compound according to claim 1.

5. The synthetic non-immunoglobulin antitumor compound relating to the structure of an immunoglobulin of claim 1, wherein the compound comprises the structure of

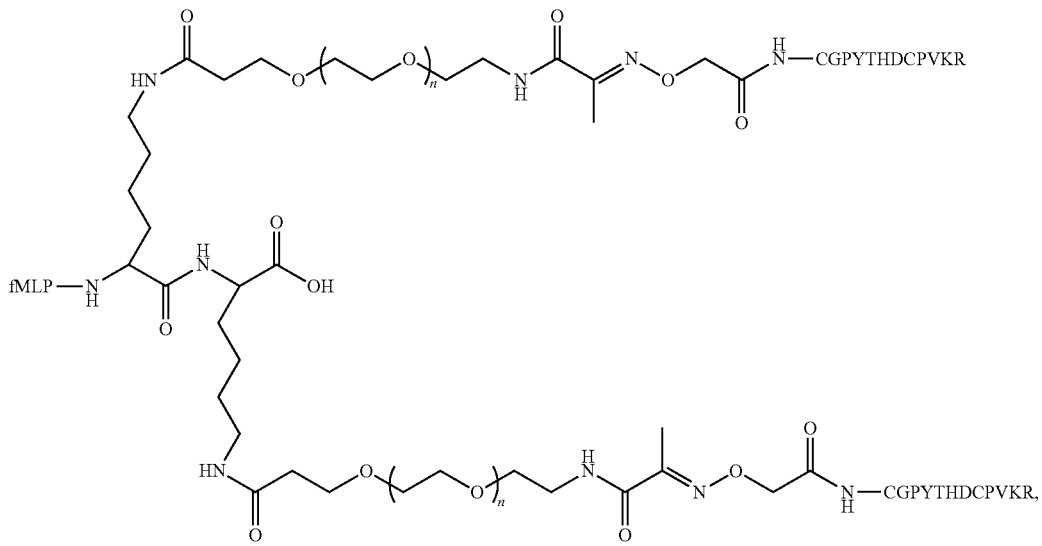

wherein the peptide CGPYTHDCPVKR consists of amino acids 5-16 of SEQ ID NO: 13.

6. A method of treating of a pharmaceutical colon cancer, head and neck cancer, ovarial cancer, pancreatic cancer, non-small cell lung cancer, breast cancer or glioblastoma cells that carry the EGFR marker, in a patient in need thereof, said method comprising administering to said patient an effective amount of the pharmaceutical composition according to claim 4.

7. A method of treating breast cancer, pancreatic cancer, ovarian cancer, NSCLC or lymphoma or other pathogenic cells that carry an ErbB-2 receptor (Her-2), in a patient in need thereof, said method comprising administering to said patient an effective amount of the pharmaceutical composition according to claim 4.

8. A method of treating ovarian cancer Of cells that carry a Fibroblast Growth Factor Receptor (FGF receptor), in a patient in need thereof, said method comprising administering to said patient an effective amount of the pharmaceutical composition according to claim 4.

9. A method of treating multiple peritoneal tumors of gastric cancer cells that carry an Integrin including Alpha- 3-beta-1 Integrin and Alpha-4-beta-1 Integrin, in a patient in need thereof, said method comprising administering to said patient an effective amount of the pharmaceutical composition according to claim 4.

10. A method of treating breast cancer cells that carry the human beta-galactoside-binding lectin Galectin-3 (Gal-3), in a patient in need thereof, said method comprising administering to said patient an effective amount of the pharmaceutical composition according to claim 4.

11. A method of treating human cancers that have a VEGFR, in a patient in need thereof, said method comprising administering to said patient an effective amount of the pharmaceutical composition according to claim 4.

12. A method of treating pathogenic cells that carry the EGFR marker other than colon cancer, head and neck cancer, ovarian, cancer, pancreatic cancer, non-small cell lung cancer, breast cancer or glioblastoma cells, in a patient in need of treatment by administering an effective amount of a with the pharmaceutical composition according to claim 4.

13. A method of treating pathogenic Cells that carry the ErbB-2 receptor/(Her-2), other than colon cancer, head and neck cancer, ovarian, cancer, pancreatic cancer, non-small cell lung cancer, breast cancer or glioblastoma cells, in a patient in need of treatment by administering an effective amount of a with the pharmaceutical composition according to claim 4.

14. A method of treating pathogenic cells that carry a Fibroblast Growth Factor Receptor (FGF receptor), other than colon cancer, head and neck cancer, ovarian, cancer, pancreatic cancer, non-small cell lung cancer, breast cancer or glioblastoma cells, in a patient in need of treatment by administering an effective amount of a with the pharmaceutical composition according to claim 4.

15. A method of treating pathogenic cells that carry an Integrin including Alpha-3-beta-1 Integrin and Alpha-4-beta-1 Integrin, other than colon cancer, head and neck cancer, ovarian, cancer, pancreatic cancer, non-small cell lung cancer, breast cancer or glioblastoma cells, in a patient in need of treatment by administering an effective amount of a with the pharmaceutical composition according to claim 4.

16. A method of treating pathogenic cells that carry the human beta-galactoside-binding lectin Galectin-3 (Gal-3), other than colon cancer, head and neck cancer, ovarian, cancer, pancreatic cancer, non-small cell lung cancer, breast cancer or glioblastoma cells, in a patient in need of treatment by administering an effective amount of a with the pharmaceutical the composition according to claim 4.

* * * * *